United States Patent [19]

Christensen et al.

[11] Patent Number: 5,314,878
[45] Date of Patent: May 24, 1994

[54] COMPOSITION FOR REMOVING OR INACTIVATING HARMFUL COMPONENTS IN BLOOD OR OTHER EXTRACELLULAR BODY FLUIDS

[76] Inventors: Henry M. Christensen, Roskilde; Hans B. Andreasen, Viby, both of Denmark

[73] Assignee: A/S af 18. juni 1990, Roskilde, Denmark

[21] Appl. No.: 806,206

[22] Filed: Dec. 13, 1991

[30] Foreign Application Priority Data

Jun. 14, 1989 [DK] Denmark ............................ 2913/89

[51] Int. Cl.$^5$ .................. A61K 31/715; C08B 31/10; C07D 321/00; C07D 321/10
[52] U.S. Cl. ........................................ 514/59; 514/54; 514/832; 514/833; 549/349; 549/351; 549/352; 549/353; 549/334; 549/369
[58] Field of Search ............... 514/54, 59, 832, 833, 514/58; 549/349, 351, 352, 353, 334, 369

[56] References Cited

U.S. PATENT DOCUMENTS

| | | | |
|---|---|---|---|
| 3,997,565 | 12/1976 | Kauer | 549/349 |
| 4,080,337 | 3/1978 | Cram | 549/351 |
| 4,104,275 | 8/1978 | Kauer | 549/351 |
| 4,113,739 | 9/1978 | Trucks et al. | 549/369 |
| 4,436,923 | 3/1984 | Pacey et al. | 549/352 |
| 4,474,963 | 10/1984 | Gokel | 549/352 |
| 4,562,272 | 12/1985 | Harrison et al. | 549/352 |
| 4,570,004 | 2/1986 | Lagow et al. | 549/352 |
| 4,631,119 | 12/1986 | Gokel et al. | 549/352 |
| 4,767,614 | 8/1988 | Scarpa et al. | 514/59 |
| 4,777,270 | 10/1988 | Urban | 549/349 |
| 4,794,000 | 12/1988 | Ecanow | 514/59 |
| 4,810,696 | 3/1989 | Anzalone | 514/59 |
| 5,089,479 | 2/1992 | Kriuan et al. | 514/59 |
| 5,100,879 | 3/1992 | Ueno et al. | 514/59 |

FOREIGN PATENT DOCUMENTS

| | | |
|---|---|---|
| 97960 | 1/1984 | European Pat. Off. . |
| 251459 | 1/1988 | European Pat. Off. . |
| 279557 | 8/1988 | European Pat. Off. . |
| 187360 | 12/1984 | Hungary . |
| 8901476 | 2/1989 | World Int. Prop. O. . |

OTHER PUBLICATIONS

Yamanouchi Seiyaku K. K. et al., Patent Abstracts of Japan, vol. 3, No. 43, C 96, abstract of JP 54-16494, published Feb. 7, 1979.

E. Weber, "Phase Transfer Catalysts", Merck Schuchardts publications, pp. 68–69.

Primary Examiner—Ronald W. Griffin
Attorney, Agent, or Firm—Wegner, Cantor, Mueller & Player

[57] ABSTRACT

A composition for removing or inactivating harmful components including virus from blood or other extracellular liquids comprises a crownether compound substituted on a polysaccharide, preferably dextrane. The composition may be soluble in water, preferably for intraveneous application, or insoluble for extracorporeal application.

13 Claims, 1 Drawing Sheet

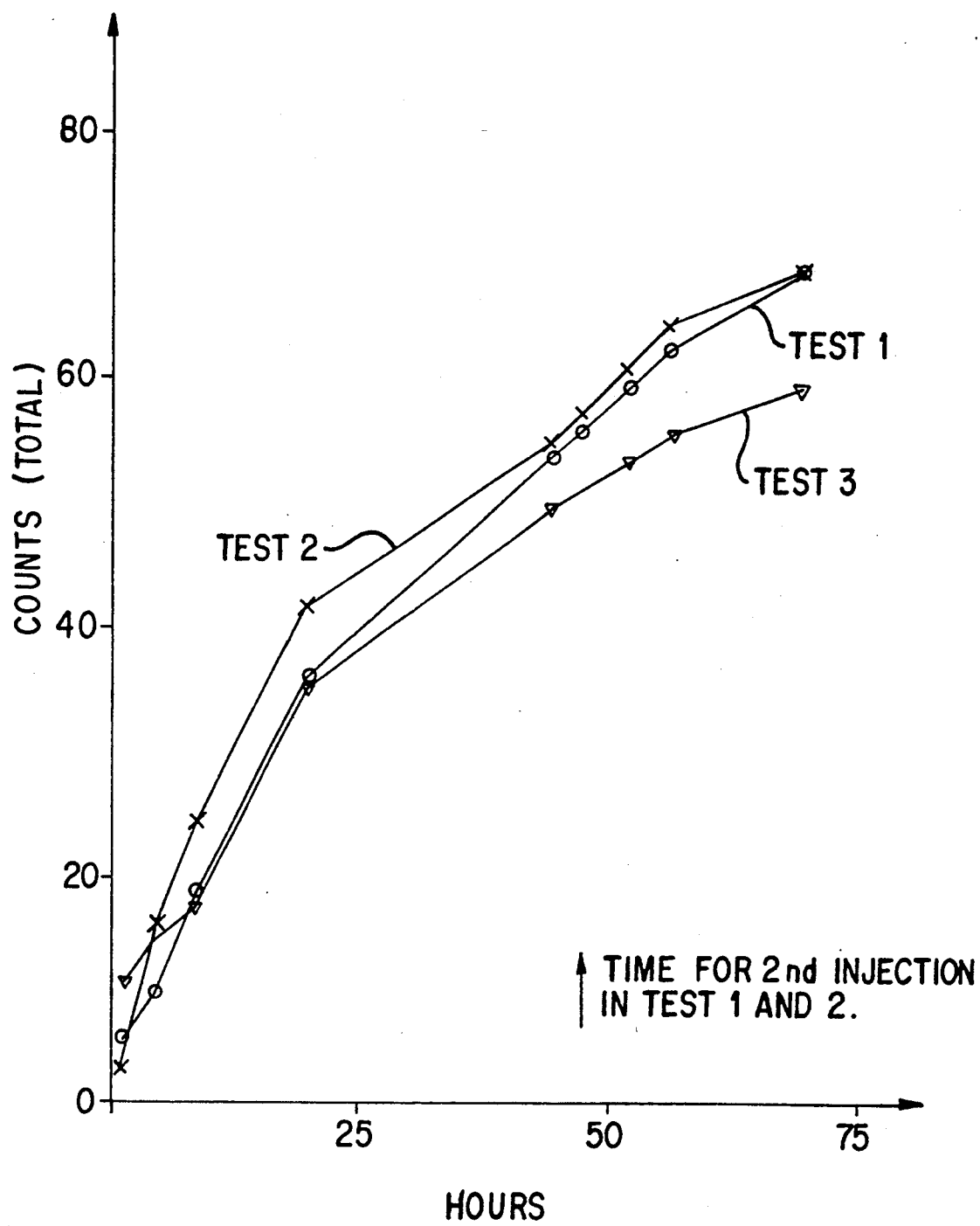

COMPOSITION FOR REMOVING OR INACTIVATING HARMFUL COMPONENTS IN BLOOD OR OTHER EXTRACELLULAR BODY FLUIDS

The present invention concerns a composition for removing or inactivating harmful components, including virus, in blood or other extracellular body fluids in humans or animals, comprising a crownether compound able to bind said component, which crownether compound has been substituted on a polysaccharide.

The term "crownether compound" in this specification and in the attached claims is used in the widest meaning of the term, viz. as comprising not only coronand compounds, but also podand compounds and cryptand compounds.

A description of coronand, podand and cryptand compounds may be found in Merck-Schuchardts publication: E. Weber "Phase Transfer Catalysts" and in the literature cited or referred to therein:

A further description of these types of compounds may be found in the following articles, all having the title: "Progress in Crown Ether Chemistry": F. Vögtle, E. Weber and U. Elben, Kontakte 2, (1980), page 36 ff; E. Weber and F. Vögtle, Kontakte 1 (1981), page 24 ff; E. Weber, Kontakte 1 (1982), page 24 ff; Kontakte 1 (1983), page 38 ff; as well as Kontakte 1 (1984), page 26 ff.

Said literature is incorporated herein by reference.

The crownether compounds first synthesized was of the type 18-crown-6, meaning they comprised the following ring:

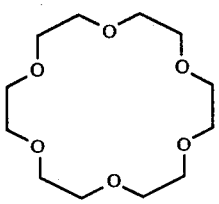

but since then other compounds of this type have been prepared some of which having a greater amount of hetero atoms while others having a smaller amount of hetero atoms.

The term "coronands" comprises also compounds of this type in which the oxygen atoms have been completely or partly replaced by sulphur, nitrogen or phosphor atoms. The term further comprises such compounds in which groups of various composition and structure have been substituted on or condensed to the ring.

The term cryptand is used to cover corresponding compounds having bi- or polycyclic ring systems having arbitrary hetero atoms, while podand compounds are open chained coronand/cryptand analogs.

It has been suggested reserving the term "crownether" to designate coronand compounds in which all hetero atoms are oxygen, but in the present specification and the attached claims the term crownether is used, as already mentioned, in the common broad sense, meaning covering all coronand, podand and cryptand compounds.

Several applications have been suggested for crownether compounds.

Most of these suggested applications have been based on the fact that, dependent on the characteristics of the individual compounds, such as dimensions of rings and cavities, the compounds are able to bind, often with high selectivity, not only cations but also anions and non-charged organic molecules. Several of these suggested applications have been related to the exploitation of the compounds in chemical syntheses where they may have a catalytic effect. In connection with such applications it has been suggested immobilizing the crownether compounds by attaching them to polymer resins, especially polystyrene, with the view of minimizing the consumption of relatively expensive crownether compounds.

Also several other applications within the technical field have been suggested.

Besides, it has been reported that benzo-crownethers such as benzo-15-crown-5-derivatives and dibenzo-30-crown-10 have an anti-coccocidal activity in tissue culture tests (George R. Brown and Allan J. Foubister: J. Med. Chem. 1983, 26, 590–592). However, no in vivo effect was demonstrated when the compounds were fed to poultry admixed in the fodder.

Also U.S. Pat. No. 3,997,565 discloses that certain chrownethers in vitro show antivial effect, for which reason the compounds have been suggested inter alia as desinfectants. No therapeutic use is mentioned in said patent specification.

In the first of the above cited articles E. Weber states that the anti-bacterial and anti-viral effect of certain crownether compounds is due to their ability of complexing metals, but at the same location it is stated that real application in the physiological-pharmacological field is still out of the range.

Hungarian patent specification No. 187 360 discloses a process for producing certain cyclodextrin-crownether derivatives. It is stated that if the cyclodextrin molecule and the crownether molecule are attached together through a side-chain containing amino or carbonyl groups, the resulting molecule may be able to complexing saltlike organic compounds since a complex bond is formed both with the cation and the apolar group of the organic anion. It is asserted that this complex formation can be utilized for amending pharmacocinematic characteristics of organic molecules having ionic bond. There is no suggestion that the cyclodextrin-crownether derivatives as such should be applicable as pharmaceuticals and nothing seems to be mentioned as to their compatibility within the human body.

The specification of WO-publication number 89/01476 deals with special crownether compounds, namely tetra-aza compounds and metal complexes thereof as well as the use therof for diagnostic purposes or for obtaining a cytotoxic action, preferably after complexing with radioactive atoms. The possibility of connecting these crownethers to other molecules such as proteins, especially antibodies, peptides or carbonhydrates is mentioned as a theoretical, non-substantiated possibility. It is not indicated what advantages could be expected by such purely hypothetical attachment, apart from the case where said attachment is to an antibody. Since the only therapeutical activity mentioned is a cytotoxic effect it is, on the basis of the explanation given below, obvious that an attachment to carbon hydrates only comes into consideration with low molecular weight carbon hydrates. A product obtained by attachment to for example polysaccharides has actually no or only a small cytotoxic activity per se.

The reason why crownethers have not yet found medical or therapeutic application is that free crownethers as such are extremely toxic towards mammalians and humans.

It has now turned out that the toxicity of crownethers is drastically diminished when they are attached to a polysaccharide, whereas their, sometimes very specific, ability of binding cationes, aniones or non-charged molecules is maintained.

It has further turned out that it is possible to produce crownether-polysaccharide condensation products which can be administered intraveneously or which extracorporally can be contacted with a stream of blood without the risk that bound crownether compounds be liberated as toxic, free crownether compounds.

By the invention it is possible to benefit from the high selectivity of the crownether compounds to the substances bound thereby. Based on knowledge as to the size and structure of the molecules as well as other characteristics of the substance or the substances which in each individual case shall be removed from blood or other extracellular body fluids, and possibly on the basis of simple tests a suitable crownether can be selected or synthesized for binding especially said substance or substances.

The composition according to the invention is thus suitable for treatment of humans or animals challenged by for example the following: Rhinovirus 1A, 2, 14 or other types, polio-2, Coxsackie-A 21, Coccidia, influenza or swine herpes. Moreover, it is suitable for removing $NH_4^+$-ions as well as primary, secondary and tertiary amines and compounds derived thereof from body fluids, when the natural elimination thereof is impaired due to organ deficiencies. The composition is also suitable for treating poisoning by binding and preferably removing iones of e.g. the following metals: Pb, Ag, Hg, Au, Cd, Cu, Zn, Na and K as well as radio active Cs.

The polysaccharide on which the crownether compound is substituted can be hydroxy-ethylstarch, inuline, etc. but is preferably dextrane.

A preferred embodiment of the composition according to the invention is characterized in that the polysaccharide is dextrane having a molecular weight of $M_w$ between 1000 and 120 000. Such a composition is soluble in water and can be administered intravenously.

By normal function of the kidnies most of the dextrane crownether compound will be excreted unaltered after some hours, entraining components which the crownether compound has caught while present in the extracellular liquid The invention does not consist of and is not limited by any theory concerning the drastical reduction of the toxicity of the crownether compound by the attachment to polysaccharides, especially dextrane, but it is assumed that it is important that the crownetherpolysaccharide compound remains in the extracellular liquid of the body and in contrast to free crownethers it does not influence those parts of nerves or organes where especially the ion binding ability of the crownethers would cause toxic damages.

On this basis it will be obvious that the crownether polysaccharide derivatives used in the composition according to the invention are of another type than the cytotoxic substances mentioned in the above WO-publication since it must be assumed that these substances must pass into the cells through the walls thereof from the extracellular liquid to be able to perform their cytotoxic activity.

By the embodiment in which the composition shall be administrated intravenously dextrane is, as mentioned, the preferred polysaccharide. This is not only because substantial experiences have been obtained as to the excretion of dextrane through the kidnies, viscosity characteristics etc., but also because the possibility of producing products substituted by crownethers hitherto has been especially studied by the present inventors using dextrane.

The water soluble compositions according to the invention may alternatively be used for extracorporal treatment of a blood stream, inserting a membrane between the blood stream and a solution of the water soluble composition according to the invention, which membrane under the circumstances utilized, enables the removal of harmful components from the blood stream without crownether compound passing into the blood.

Extracorporal treatment of a stream of blood can also be performed using a water insoluble form of the composition according to the invention, preferably a dextrane made water insoluble by cross linking, to which crownether is attached Such an insoluble composition is contacted with the stream of blood and takes up harmful components therefrom without the crownether compounds passing over into the blood.

When the polysaccharide is a dextrane it has proven suitable to have the crownether compound substituted thereon in an amount of up to 25 percent by weight, calculated on the substituted dextrane compound.

In the composition according to the invention the polysaccharide is, as stated, substituted with coronand, podand or cryptand compounds but a special interest attaches to polysaccharides, especially dextranes, substituted with coronand compounds, since the experimentel work using these compositions is most advanced.

A preferred composition according to the invention therefore comprises a coronand compound substituted on a polysaccharide and is characterized in that the substituting coronand groups are of a type which can be illustrated by the formula:

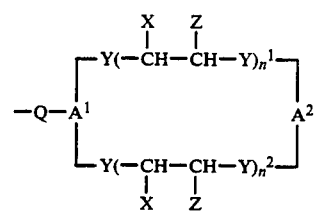

in which Q designates a group forming a bridge to the polysaccharide, and which typically can be a hydrocarbon chain which may serve as a so-called spacer and typically has 1-20 carbon atoms, wherein $A^1$ and $A^2$ which may be the same or different each is a group of one of the formulae:

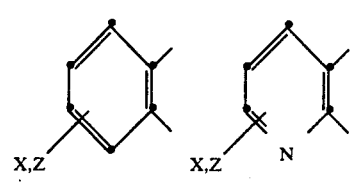

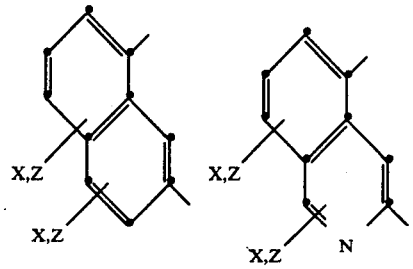

$n^1$ and $n^2$ may each independently be an integer between 0 and 20 provided that $n^1$ and $n^2$ cannot both simultaneously be 0, the symbols Y can be the same or different and is

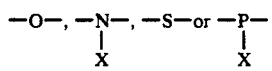

the symbols X can be the same or different and each is hydrogen or a substituent conventional in coronand compounds, for example as mentioned in U.S. Pat. No. 3,997,565 (incorporated herein by reference), the symbols Z have the same difinition as X but are in the individual compound independent of the actual significance of X, or one or more pair of the symbols X and Z designates together with C-atoms in the coronand ring and possibly together with Y one, possibly two, hydrocarbon rings or heterocyclic rings, preferably benzen rings or pyridine rings.

When Y is

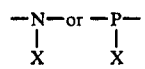

interesting compositions comprise compounds in which the X'es bound to N or P are hydrogen.

Especially interesting compounds according to the invention also comprise such wherein the coronand groups are of the above formula, in which the symbols Y do not all represent nitrogen, when $n^1+n^2=2$.

It has turned out that dextrane on which are substituted O-carbonylbenzo-18-crown-6-groups of the formula:

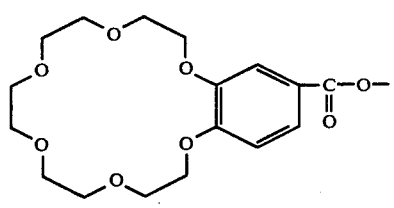

can be prepared, having a high degree of substitution, and that these substituted dextrane compounds do not have any substantial toxicity when tested e.g. on mice. Further they can be dissolved in water in sufficient concentration without the viscosity of the solution being too high for intraveneous infusion.

Also interesting are polysaccharides, especially dextran, substituted with O-hydroxy-ethylbenzo-18-crown-6-groups having the formula:

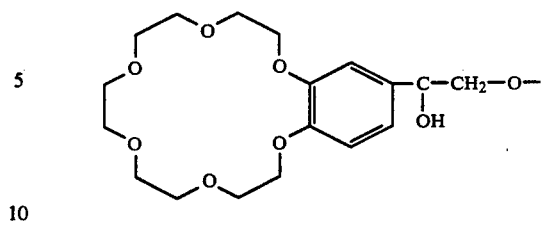

The ability of crownethers to bind iones and non-charged molecules is due to their special molecular structure. Reference is made to the above cited articles of E. Weber and the references listed therein for a more detailed explanation of this subject.

Not only ions or molecules fitting exactly in the rings or cavities of the crownethers are bound Also molecules having special portions corresponding to the crownether in question can be bound. Moreover, structures can be formed in which the crownether groups are arranged as layers between which larger molecules can be sequestered.

By choosing crownethers having suitable sizes of the rings, and as far as podands is concerned also suitable chain length, or by applying substitution or fusion for amending the effective dimensions of the rings and chains as well as their rigidity it is possible for a skilled person to synthesize crownethers being very specific for a certain task. Thus, for instance, polysaccharides on which benzo-18-crown-6 is substituted are efficient for removing or inactivating polio-2 and Coxsackie-A21 virus, whereas polysaccharides having benzo-15-crown-5 may be used for removing or inactivating $NH^{4+}$.

The fact that the crownethers in the composition according to the invention are substituted on a polysaccharide may in certain cases involve that the binding or absorption ability of the crownethers for sterical reasons is somewhat decreased. However, said decrease can be avoided by using spacer groups Q having a certain length and thereby creating a distance between the crownether structure and the polysaccharide skeleton.

The crownethers can be attached to the polysaccharides using substitution methods based on chemical reactions known per se.

For obtaining crownether compounds which can react with OH-groups in the polysaccharide, one has incorporated for instance in the 4'-position of benzo-18-crown-6, i.a. the following groups:

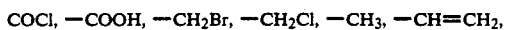
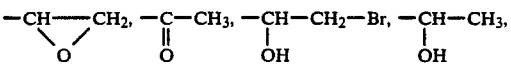

Several crownether compounds are commercially available or may be produced using methods described in the above cited literature.

Among crownether compounds regarded as interesting in connection with the present invention, besides those especially mentioned above, special emphasize is made on benzo-19-crown-6 and benzo-15-crown-5 which e.g. is suitable for producing products suitable for removing $NH^{4+}$ from blood, and benzo-12-crown-4. The reaction between the crownether compound disposing of a reactive group, and the polysaccharide is preferably performed in a solvent comprising pyridine and/or dimethylformamide.

The composition according to the invention may comprise the dextrane-crownether-products as the sole component or mixed with adjuvants conventional in pharmaceutical preparations for injection or infusion. The composition will preferably be marketed as a powder to be dissolved in physiological saline before application or in liquid injectable form.

The dose to be administered will in each individual case be determined by the physician or veterinarian and depends on the character and severety of the illness and the condition of the patient, etc.

BRIEF DESCRIPTION OF THE DRAWING

The drawing illustrates the accumulated counts from the radioactivity measurements as functions of the time.

To illustrate processes for producing crownether-polysaccharides for use in the composition according to the invention the below Examples are given. These Examples report synthesizes and analysis performed at Forsøgsanlæg Risø, Roskilde, Denmark. It should be remarked the processes and results described in said Examples are not the result of any optimization of the process.

EXAMPLE 1

Manufacture of dextrane-O-carbonylbenzo-18-crown-6

4′-Chlorocarbonylbenzo-18-crown-6 is produced after Bourgain, Wong, Hui and Smid, J. Am. Chem. Soc. 97:12 (1975), 3462–67, The yield is quantitative.

36 g Dextran (T40, that means molecular weight approximately 40 000) corresponding to 0.22 mol monomer (glucose) is suspended in 250 ml pyridine. Using stirring and by heating in an oil bath at 65°–70° C. 22.1 g 4′-chlorocarbonylbenzo-18-crown-6, corresponding to 0.06 mol, is added dissolved in 75 ml pyridine. The reaction mixture is cooled and precipitated with acetone. The precipitated syrup is dissolved in water and once more precipitated using acetone. The precipitate is redissolved in water and dialysed for one day. The dialysed product is lyophilized. Yield 34 g corresponding to 61% of the theoretical yield.

The product is analysed using mass spectroscopy, NMR and HPLC.

The content of chemically bound crownether compound in the product is 17.4%, content of free crownether compound in the product: 0.3% (calculated on basis of UV-graph).

By a similar method a product was prepared having a content of crownether compound attached to dextrane of approximately 8%.

EXAMPLE 2

Production of dextrane-hydroxyethylbenzo-18-crown-6

4′-(2″-bromo-1″-hydroxyethyl)-benzo-18-crown-6 is preparred from 4′-vinylbenzo-18-crown-6 by reaction with N-bromoacetamide in dioxane. Yield of the crude substance 90%.

Three solutions were prepared:

I: 5 g dextrane (T20, i.e. dextrane having a molecular weight of 20 000) corresponding to 0.03 mol monomer (glucose) is dissolved in approximately 10 ml water.

II: 3.5 g 4′-(2″-bromo-1″-hydroxyethyl)-19-crown-6 corresponding to 0.008 mol is dissolved in 10 ml water.

III: 4.3 g sodium hydroxide corresponding to 0.011 mol, is dissolved in 10 ml water.

The solution I is heated to 60° C. and one third of the solution II and one third of solution III are added. The mixture is agitated at 60° C. for 15 minutes whereupon one third of each of the original solutions II and III is added again, and after further fifteen minutes the remaining third of each of the two solutions is added. The temperature is raised to 70° C. and the reaction mixture stirred for further approximately two hours. The mixture is cooled at ambient temperature and precipitated using acetone. The precipitated syrup is dissolved in water and precipitated once more with acetone. The syrup is redissolved in water, acidified with 2 N HCl to pH 4.5 and thereafter precipitated using alcohol. The precipitated product is redissolved in water, dialysed for 24 hours and lyophilized.

Yield 3.5 g corresponding to 45% of the theoretical yield. The substance is subjected to HPLC. The contents of crownether compound bound to dextran is 1.45% and the contents of free crownether compound 0.12%. Purety: 96.5%.

Test of the Composition

Toxicity and Elimination

T40-Dextrane-0-carbonylbenzo-18-crown-6 was prepared according to the method of Example 1 to obtain two products having different levels of substitution. One product (A) had a level of substitution of 8%. The content of free crownether compound in this product was not analysed. The other product (B) had a degree of substitution of 15% and a content of crownether compound not chemically bound of 0.3%.

The product A was at a concentration of 1% injected intraveneously in mice which each received a dose of 0.4 ml corresponding to $32 \times 10^{-4}$ g crownether. The mice did not show any sign of illness. The urine was collected and subjected to UV analysis which showed that the dextran-O-carbonylbenzo-18-crown-6 compound was excreted substantially completely after 3–5 hours.

The product B was tested similarily but at a concentration of 10%. The dose was here 0.4 ml corresponding to $6.0 \times 10^{-3}$ g crownether compound. The content of free crownether compound in this dose amounted to $1.2 \times 10^{-4}$ g. Several animals were subdued after having received this dose and had bristled furs for approximately 30 minutes, but thereafter they did not shown any symptoms.

Two series of comparison tests were also made with the crownether monomer.

In the first test benzo-18-crown-6 was injected as aqueous solution having a concentration of 0.8% at a dose of 0.4 ml per animal, corresponding to $32 \times 10^{-4}$ g crownether. The animals died immediately before the injection was completed.

In the other comparison test benzo-18-crown-6 was used at a concentration of 0.08%. Also here the dose was 0.4 ml corresponding to $3.2 \times 10^{-4}$ g crownether. In this case heavy convulsions appeared lasting for approximately 15 minutes, however, the animals survived.

The reaction which was experienced by administration of the product (B) is probably due to the content of free crownether in the product and can be avoided using a more extensive cleaning of the product.

By administration of $3.2 \times 10^{-4}$ g benzo-18-crown-6 as the pure compound a significantly heavier reaction is thus obtained than by the above described test using product (B), where an amount of $1.2\times 10^{-4}$ g of the same compound in non-bound condition was introduced as impurity. This substantiates the above assumption that the reaction experienced using product (B) is not due to the crownether bound to the dextrane but is due to the amount present as not chemically bound impurity.

COUNTERACTING VIRUS INFECTIONS

Tests performed by Statens veterinære Institut for Virusforskning, Lindholm, Denmark.

TEST 1

The test was performed using foot- and -mouth disease virus, type A on young mice (3-4 days of age). With the virus suspension 2 identical dilution series (series 1 and 2) were produced comprising dilutions from $10^{-1}$ to $10^{-8}$. Before inoculating the mice, each dilution sample was mixed with an equal volume of one of the following:

| 1. | Phosphate buffer (virus control) | series 1 |
|---|---|---|
| 2. | 5% aqueous solution of dextrane-crownether compound prepared according to Example 1 and having 17.4% bound crownether | series 2 |

Each mixture was inoculated intraperitoneally into 8 young mice. Dose 0.2 ml/mouse. The test was repeated twice using 2 different virus preparations $(1/486)\cdot10^{-4}$ and $(1/63)\cdot10^{-4}$ corresponding to 1 and 8 mice-patogen units (run A and run B, resp.).

The following results were obtained (virus titres):

| | | Run A | Run B |
|---|---|---|---|
| 1. | Virus control | 7.5 | 6.5 |
| 2. | Virus + dextrane-crownether | 7.0 | 5.0 |

The titre which reflects the contents of infective virus in the mixture, is expressed by the negative logarithm of the virus dilution corresponding to a 50% mortality of the inoculated mice. The reliability of the procedure is usually around ±0.5. This means that a difference between titres must be more than 1 to be significant. Thus, in run A the difference between the virus control (1) and the virus +dextrane-crownether (3) is not significant, whereas run B shows that the dextrane-crownether compound impedes the viral activity.

TEST 2

40 Guinea pigs were inoculated simultaneously using foot-and-mouth desease virus, type A, Holland. The inoculation was performed by injecting a virus suspension intracutaneously in one planta. Each Guinea pig received approx. 500 infective Guinea pig units.

The inoculated Guinea pigs were divided into two groups of each 20 animals. In three consecutive days, starting on the day of inoculation, one of these groups was treated with physiological saline whereas the other group was treated with a 5% by weight solution of dextrane-crownether compound (prepared according to Example 1, 17.4% by weight crownether).

Each animal received two subcutaneous injections each day. Each injection was 1 ml.

The animals were checked the 3rd, 4th and 5th day after inoculation and the development of the desease was evaluated on basis of the number of blisters on the three plantae where no inoculation had been made. An antiviral effect manifested itself as a reduction of the numbers of blisters.

The following results were obtained:

Number of blistes as percentage of the maximum number:

| | 3rd day | 4th day | 5th day |
|---|---|---|---|
| Physiological saline | 25 | 66 | 100 |
| Dextrane-crownether | 15 | 43 | 86 |

From the above results it appears that a reduction of the number of blisters was obtained by injection of the dextrane-crownether compound. Based on knowledge as to the rate of renal elimination of the dextrane-crownether compound it is most likely that an even more efficient anti-viral effect would have been experienced, if the treatment had been continued beyond the 3rd day.

TEST 3

40 Guinea pigs were simultaneously inoculated using foot-and-mouth desease virus, type C, Turup. The inoculation was performed by injecting a virus suspension instracutaneously in one planta. Each Guinea pig received approx. 500 infective Guineas pig units.

The inoculated Guinea pigs were divided into two groups of each 20. One of the groups was treated with physiological saline whereas the other was treated with a 3.75 percent by weight solution of dextrane-crownether compound in physiological saline. The dextrane-crownether-compound was the one preparred in Example 1 having 17.4 percent by weight bound crownether.

The treatment was performed using the following scheme:

On the very date of inoculation as well as on the first, second and third day after the inoculation each Guinea pig was injected using ½ ml liquid intracordially and $2\times2$ ml subcutaneously. The injections were made at 9 a.m., at noon and at 3 p.m.

The animals were checked daily and the development of the desease was evaluated on basis of blisters formed on the plantal in which no inoculation had been made.

The following results were obtained:

Number of blisters at various days after inoculation, indicated as percentages of the maximum number counted:

| | 3rd day | 5th day | 6th day |
|---|---|---|---|
| Physiological saline | 0 | 8 | 100 |
| Dextrane-crownether (3.75%) | 0 | 2 | 90 |

The above results show that the dextrane-crownether compound exhibited an antiviral activity at all three days were the development of the disease was evaluated.

Also in connection with this tests it applies that it seems most likely that if the treatment had been continued for more than the first three days substantial lower counts of blisters would have been found and possibly a complete recovering experienced on the 5th and 6th day in the group receiving the dextrane-crownether compound.

Complexing Capability

A: By diffusion tests using a membrane cell in which a dextrane-benzo-18-crown-6 product, as the one prepared according to Example 1, was present in aqueous, alcohol containing solution on one side of the membrane, it has turned out that the capability of complexing metals, such as sodium ions, characteristic of the free crownether has been maintained in the crownether product substituted on dextrane.

B: Test made at Forsøgsanlæg Risø, Roskilde, Denmark:

2.5 g dextrane-hydroxyethylbenzo-18-crown-6, prepared according to Example 2 above, was dissolved in 50 ml aqueous cesium-containing solution having 10 μg $Cs^{134}$/ml.

The resulting solution was transferred to a hose for dialysis having a pore radius of approximately 1.5 nm. The hose with its content was placed in a graduated glass containing 150 ml aqueous solution comprising 10 μg $Cs^{134}$/ml which glass was provided with mechanical stirring.

In the dialysis hose 2 ml solution was added containing 10 μg $Ca^{134}$/ml+a trace of $Cs^{137}$ (approx. 20 000 Bq). After 12 hours samples taken from the liquid inside the dialysis hose and from the liquid outside the hose in the graduated glass, resp., were measured by means of a gamma counter operating at 0.66 MeV, to determine the ratio of the Cs concentration inside the dialysis hose to the Cs concentration outside the hose. On the basis of these determinations the corresponding amounts of Cs in the two liquids were calculated. The results appear from the following table:

|  | Cs conc. inside hose/ Cs conc. outside hose | Cs in liquid | |
|---|---|---|---|
|  |  | inside the hose | outside the hose |
| Initially | 1 | 520 μg | 1500 μg |
| After 12 h | 1.2 | 658 μg | 1362 μg |

The above results prove that the dextrane-crownether compound tested has a substantial capability of catching and binding cesium ions. It was not checked whether equilibrium had actually been obtained after 12 h or if even more convincing results would have been obtained in case it had been possible to run the test for more than the 12 hours.

Elimination of $Cs^{137}$ from blood

Tests were preformed at Forsøgsstation Risø, Department of Health, Roskilde, Denmark, to investigate the ability of the dextrane-crownether compounds to remove radioactive cesium, $Cs^{137}$, from the blood of mice.

Three tests were run, each using five mice.

As basis solution for use as injection liquid or for use as basis for the preparation of such, an aqueous 0.9% sodium chloride solution was used containing $Cs^{137}$ in an amount corresponding to 3000 Bq/ml.

In each test the mice were kept in a cage, the bottom of which was a net below which a funnel was arranged for collecting the urine of the mice. After each collection of urine the bottom was flushed with water, and urine plus flushing water were collected and diluted with water to 20 ml before the radioactivity were determined by means of a Geiger counting apparatus.

TEST 1

By this test each mouse was injected with 0.1 ml af the basis solution and thus received 300 Bq $Cs^{137}$. The time for this injection, below designated $t_o$, was 11:30.

After one hour each mouse was injected with 0.4 ml of a 6 w/v-% aqueous solution of the dextrane-O-carbonylbenzo-18-crown-6-product produced according to Example 1, corresponding to 24 mg of this product per mouse.

Collection of urine with subsequent determination of radioactivity was initiated one hour and 24 minutes, corresponding to 1.35 hours, after $t_o$ and was continued as it appears from Table I below.

47.81 hours after $t_o$ a further injection of 0.5 ml of the 6%'s dextrane-crownether-solution was made on each mouse and the collection of urine and determination of radioactivity therein were continued.

The results appear from Table 1 below.

TABLE I

| Time/date | | time after $t_o$ (hours) | radioactivity (counts) in urine + flushing water |
|---|---|---|---|
| 12:54 | 19.6.90 | 1.35 | 6978 |
| 16:20 | 19.6.90 | 4.83 | 3684 |
| 20:23 | 19.6.90 | 8.88 | 8280 |
| 7:34 | 20.6.90 | 20.07 | 17001 |
| 8:25 | 21.6.90 | 44.92 | 17368 |
| 11:17 | 21.6.90 | 47.78 | 2213 |

Further dextrane-crownether-injection, following which new $t_o$ was 11:34 the 21.6.90.

| 15:58 | 21.6.90 | 4.63 | 3533 |
|---|---|---|---|
| 20:00 | 21.6.90 | 8.67 | 2937 |
| 9:37 | 22.6.90 | 22.28 | 6391 |

The results are, in the form of accumulated values for radioactivity, included in Table 4 below and are incorporated in the drawing.

TEST 2

At this test the injection solution was a mixture of 2 ml of the above mentioned $Cs^{137}$-containing solution and 8 ml of the dextrane-crownether solution used in Test 1.

Each mouse was injected with 0.5 ml of the mixture and thus received 300 Bq $Cs^{137}$ and 24 mg dextrane-crownether. Collection of urine and further crownether injection (0.5 ml 6% solution) was made as in Test 1 as it appears from Table II below.

TABLE II

| Time/date | | time after $t_o$ (hours) | radioactivity (counts) in urine + flushing water |
|---|---|---|---|
| 12:56 | 19.6.90 | 0.87 | 4498 |
| 16:25 | 19.6.90 | 4.62 | 11634 |
| 20:27 | 19.6.90 | 8.65 | 8566 |
| 7:37 | 20.6.90 | 19.82 | 16805 |
| 8:27 | 21.6.90 | 44.65 | 12901 |
| 11:20 | 21.6.90 | 47.53 | 2728 |

Further dextrane-crownether-injection following which new $t_o$ was 11:40 the 21.6.90.

| 16:00 | 21.6.90 | 4.33 | 3659 |
|---|---|---|---|
| 20:04 | 21.6.90 | 8.40 | 3222 |

-continued

| 9:40 | 22.6.90 | 22.08 | 4966 |

TEST 3

By this comparison test the injection solution was a mixture of 2 ml of the above mentioned basis solution containing 3000 Bq/ml $Cs^{137}$ and 8 ml aqueous 0.9% by weight NaCl-solution. Each mouse was injected using 0.2 ml of the mixture and thus received 300 Bq $Cs^{137}$.

Collection of urine was made as follows:

TABLE III

| | $t_0$ = 12:00 to 19.6.90 | | |
|---|---|---|---|
| Time/date | | time after $t_0$ (hours) | radioactivity (counts) in urine + flushing water |
| 13:18 | 19.6.90 | 1.30 | 11355 |
| 16:29 | 19.6.90 | 4.48 | 3612 |
| 20:32 | 19.6.90 | 8.53 | 2542 |
| 7:40 | 20.6.90 | 19.66 | 17414 |
| 8:30 | 21.6.90 | 44.50 | 14592 |
| 16:03 | 21.6.90 | 52.05 | 3324 |
| 20:06 | 21.6.90 | 56.10 | 2522 |
| 9:42 | 22.6.90 | 69.70 | 3455 |

In Table IV below the results obtained in Tests 1, 2 and 3 are accumulated.

TABLE IV

| Test 1 | | Test 2 | | Test 3 | |
|---|---|---|---|---|---|
| Time | Counts, total | Time | Counts, total | Time | Counts, total |
| 1.35 | 6978 | 0.87 | 4498 | 1.30 | 11355 |
| 4.83 | 10662 | 4.62 | 16132 | 4.48 | 14967 |
| 8.88 | 18942 | 8.65 | 24698 | 8.53 | 17509 |
| 20.07 | 35943 | 19.82 | 41503 | 19.66 | 34923 |
| 44.92 | 53311 | 44.65 | 54411 | 44.50 | 49515 |
| 47.78 | 55524 | 47.53 | 57139 | 52.05 | 52839 |
| 52.41 | 59057 | 51.86 | 60798 | 56.10 | 55361 |
| 56.45 | 61994 | 55.93 | 64020 | 69.70 | 58816 |
| 67.06 | 68385 | 69.53 | 68986 | | |

The accumulated results of Table IV form basis for the drawing which illustrates the accumulated counts from the radioactivity measurements as function of the time.

By a cautious evaluation and comparison of the results obtained in Test 1, 2 and 3 it can be deduced that the speed af elimination in the first 5-8 hours after the first injection is significantly increased due to the administration of the dextrane-crownethercompound.

It also appears that after the second injection a somewhat increased speed of excretion is obtained in approximately 8 hours, after which the speed of excretion falls to the level in Test 3.

It also appears that in the approximately 70 hours in which the observations to place the mice in Tests 1 and 2, which received the dextrane-crownether, excreted approximately 17% more radioacative Cs than the mice in comparison Test 3.

We claim:

1. A compound for removing or inactivating harmful components from human or animal blood or from other extracellular body fluids, comprising a crownether able to bind the harmful components, which crownether is chemically bonded to a polysaccharide selected from the group consisting of dextran, hydroxyethyl starch, and inuline.

2. Compound according to claim 1, characterized in that the polysaccharide is dextran.

3. A compound according to claim 2, suitable for intravenous administration, characterized in that the polysaccharide is dextran having a molecular weight Mw between 1000 and 120 000.

4. Compound according to claim 1 comprising a dextran made water-insoluble by crosslinking and substituted with crownether.

5. Compound according to claim 2, characterized in that the crownether compound constitutes up to 25 percent by weight of the crownether substituted dextran.

6. Compound according to claim 1, characterized in that the crownether is a coronand compound and that the substituted coronand groups are represented by the formula:

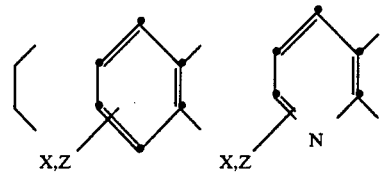

wherein Q is a hydrocarbon chain having 1-20 carbon atoms, wherein $A^1$ and $A^2$, which can be the same or different, are each a group of one of the formulae:

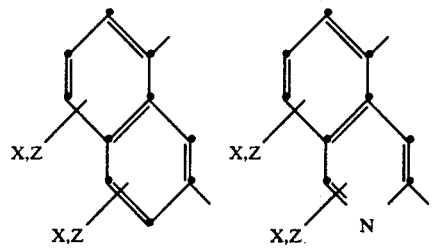

$n^1$ and $n^2$ can be the same or different and are each an integer between 0 and 20, provided that $n^1$ and $n^2$ can not be 0 simultaneously, Y can be the same or different and is

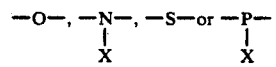

X can be the same or different and is hydrogen, Z can be the same or different and is hydrogen, or one or more pair of the symbols X and Z together with C-atoms in the coronand ring, and optionally together with Y, form one or two hydrocarbon rings.

7. Compound according to claim 6, characterized in that Y is nitrogen or phosphor, and the X attached thereto is hydrogen.

8. Compound according to claim 6, characterized in that the polysaccharide is dextran substituted with O-carbonylbenzo-18-crown-6-groups of the formula:

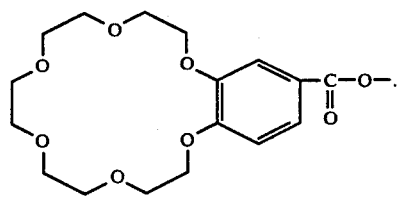

9. Compound according to claim 6, characterized in that the polysaccharide is dextran substituted with O-hydroxyethylbenzo-18-crown-6-groups of the formula:

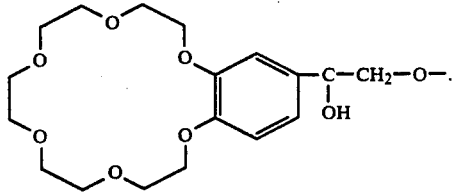

10. A process for producing dextran-O-carbonylbenzo-18-crown-6 useful in the compound according to claim 8, characterized in that dextran in pyridine/dimethylformamide is reacted with 4'-chlorocarbonyl-benzo-18-crown-6.

11. A process for producing dextranhydroxy-ethylbenzo-18-crown-6 useful in the compound according to claim 9, characterized in that dextran in an aqueous basic medium is reacted with 4'-(2''-bromo-1''-hydroxyethyl)-18-crown-6.

12. The compound of claim 6 wherein the one or two hydrocarbon rings are benzene or pyridine.

13. A pharmaceutical composition for removing or inactivating harmful components from human or animal blood or other extracellular body fluids comprising the compound according to claim 1 in combination with one or more pharmaceutically acceptable carriers or diluents.

* * * * *